US006559460B1

(12) United States Patent
Keogh et al.

(10) Patent No.: US 6,559,460 B1
(45) Date of Patent: May 6, 2003

(54) ULTRAVIOLET LAMP SYSTEM AND METHODS

(75) Inventors: Patrick Gerard Keogh, Berkshire (GB); James W. Schmitkons, Lorain, OH (US)

(73) Assignee: Nordson Corporation, Westlake, OH (US)

( * ) Notice: Subject to any disclaimer, the term of this patent is extended or adjusted under 35 U.S.C. 154(b) by 219 days.

(21) Appl. No.: 09/702,519

(22) Filed: Oct. 31, 2000

(51) Int. Cl.[7] ................................................ A61N 5/00
(52) U.S. Cl. ................................ 250/492.1; 250/504 R
(58) Field of Search ....................... 250/492.1; 426/243

(56) References Cited

U.S. PATENT DOCUMENTS 4,042,850 A 8/1977 Ury et al.
4,535,753 A 8/1985 Zayauskas
4,591,724 A * 5/1986 Fuze et al. ............... 250/492.1
4,710,638 A * 12/1987 Wood ...................... 250/492.1
4,800,090 A * 1/1989 August ...................... 426/243
4,928,040 A 5/1990 Uesaki
4,990,789 A 2/1991 Uesaki
5,136,491 A 8/1992 Kano

FOREIGN PATENT DOCUMENTS

FR 2674526 10/1992

* cited by examiner

*Primary Examiner*—John R. Lee
*Assistant Examiner*—Christopher M Kalivoda
(74) *Attorney, Agent, or Firm*—Wood, Herron & Evans, L.L.P.

(57) ABSTRACT

An ultraviolet radiation generating system and methods is disclosed for treating a coating on a substrate, such as a coating on a fiber optic cable. The system comprises a microwave chamber having one or more ports capable of permitting the substrate to travel within or through a processing space of the microwave chamber. A microwave generator is coupled to the microwave chamber for exciting a longitudinally-extending plasma lamp mounted within the processing space of the microwave chamber. The plasma lamp emits ultraviolet radiation for irradiating the substrate in the processing space. A reflector is mounted within the processing space of the microwave chamber and is capable of reflecting ultraviolet radiation to uniformly irradiate the substrate in a surrounding fashion. When the system is operating, the microwave chamber is substantially closed to emission of microwave energy and ultraviolet radiation.

15 Claims, 3 Drawing Sheets

ULTRAVIOLET LAMP SYSTEM AND METHODS

FIELD OF THE INVENTION

The present invention relates generally to ultraviolet lamp systems and, more particularly, to microwave-excited ultraviolet lamp systems configured to irradiate a substrate positioned within the microwave chamber with ultraviolet radiation.

BACKGROUND OF THE INVENTION

Ultraviolet lamp systems are commonly used for heating and curing materials such as adhesives, sealants, inks, and coatings. Certain ultraviolet lamp systems have electrodeless light sources and operate by exciting an electrodeless plasma lamp with either radiofrequency energy or microwave energy. In an electrodeless ultraviolet lamp system that relies upon excitation with microwave energy, the electrodeless plasma lamp is mounted within a metallic microwave cavity or chamber. One or more microwave generators are coupled via waveguides with the interior of the microwave chamber. The microwave generators supply microwave energy to initiate and sustain a plasma from a gas mixture enclosed in the plasma lamp. The plasma emits a characteristic spectrum of electromagnetic radiation strongly weighted with spectral lines or photons having ultraviolet and infrared wavelengths. To irradiate a substrate, the radiation is directed from the microwave chamber through a chamber outlet to an external location. The chamber outlet is capable of blocking emission of microwave energy but allows electromagnetic radiation to be transmitted outside the microwave chamber. A fine-meshed metal screen covers the chamber outlet of many conventional ultraviolet lamp systems. The openings in the metal screen transmit electromagnetic radiation for irradiating a substrate positioned outside the microwave chamber, yet substantially block the emission of microwave energy.

The electrodeless plasma lamp emits a characteristic spectrum isotropically outward along its cylindrical length. Part of the emitted radiation moves directly from the plasma lamp toward the substrate without reflection. However, a significant portion of the emitted radiation must undergo one or more reflections to reach the substrate. To capture this indirect radiation, a reflector can be provided that is mounted within the microwave chamber in which the plasma lamp is positioned. The reflector includes surfaces capable of redirecting incident radiation in a predetermined pattern toward the chamber outlet and to the substrate positioned outside the microwave chamber.

A major shortcoming of conventional systems is the inability to accurately predict the focal point or focal plane outside the microwave chamber at which the reflected ultraviolet radiation will be delivered. Another shortcoming is the reflector of the lamp system cannot be easily modified to adjust the focal point or focal plane, if known, so that the substrate can be repositioned relative to the lamp system. Further, the inability to accurately predict the focal point or focal plane limits the ability to mass produce lamp systems capable of delivering predictable radiation patterns to a substrate. A further limitation is that conventional ultraviolet lamp systems are designed to irradiate a flat surface on large-area substrates and cannot be easily adapted to uniformly irradiate substrates in a surrounding fashion. For example, conventional ultraviolet lamp systems cannot uniformly irradiate the entire circumference of round substrates.

If the plasma lamp is considered a line source of radiation, the intensity of ultraviolet radiation striking the substrate is inversely proportional to the separation between the plasma lamp and the substrate. As a result, the ultraviolet radiation is significantly attenuated when traveling from the plasma lamp on the interior of the microwave chamber to the substrate positioned outside the microwave chamber. To compensate for this loss in intensity, the microwave power must be elevated to increase the output of the plasma lamp. However, the amount of infrared radiation will likewise increase with the output of the plasma lamp. The excess infrared energy heats the substrate, the microwave chamber, and the plasma lamp. The elevation in temperature associated with the excess infrared energy can significantly reduce the lifetime of the plasma lamp and can produce additional undesirable effects.

Thus, a microwave-excited ultraviolet lamp system is needed with a configuration capable of uniformly irradiating a substrate positioned within the microwave chamber with ultraviolet radiation and that can do so without emitting significant amounts of microwave energy.

SUMMARY OF THE INVENTION

The present invention overcomes the foregoing and other deficiencies of conventional microwave-excited ultraviolet lamp systems. While the invention will be described in connection with certain embodiments, the invention is not limited to these embodiments. On the contrary, the invention includes all alternatives, modifications and equivalents as may be included within the spirit and scope of the present invention.

According to the present invention, an ultraviolet radiation generating system for treating a coating on a substrate, such as a coating on a cable or, more specifically, a coating on a fiber optic cable, comprises a microwave chamber having an inlet port capable of permitting the cable to travel within a processing space of the microwave chamber. During operation, the microwave chamber is substantially closed to emission of microwave energy and the emission of ultraviolet radiation. A microwave generator is coupled to the microwave chamber for exciting a longitudinally-extending plasma lamp mounted within the processing space of the microwave chamber. The plasma lamp emits ultraviolet radiation for irradiating the fiber optic cable traveling within the chamber. A reflector is mounted within the microwave chamber and is capable of reflecting ultraviolet radiation for irradiating the fiber optic cable as it travels within the chamber.

In certain embodiments, the microwave chamber may further include an outlet port so that the cable travels through the microwave chamber and at least partially within the processing space between the inlet and outlet ports. In other embodiments, the lamp system may also include an ultraviolet-transmissive conduit positioned within the microwave chamber generally between the inlet and outlet ports. The conduit encloses the substrate when it is positioned within the processing space of the microwave chamber. In still other embodiments, the lamp system may also include microwave chokes attached to the inlet and outlet ports and capable of reducing the emission of microwave energy from the inlet and outlet ports.

The present invention permits the substrate to be positioned directly within the microwave chamber for treatment with ultraviolet radiation. As a result, the chamber may be completely sealed to prohibit the emission of microwave energy and to eliminate the necessity of emitting ultraviolet radiation from the microwave chamber. Because the substrate, the plasma lamp, and the reflector have well-defined relative positions within the microwave chamber, the plasma lamp and reflector can be precisely located relative to the substrate for purposes of providing a predictable and reproducible pattern of radiation at and about the substrate. Because the substrate is positioned within the microwave chamber, a greater intensity of ultraviolet radiation per unit measure of microwave energy can be delivered to the substrate. As a result, the microwave energy can be reduced to deliver a given intensity of ultraviolet radiation to the substrate or the ultraviolet intensity can be optimized for improving the treatment throughput of the lamp system.

The above and other advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF PREFERRED EMBODIMENTS

The present invention relates to microwave-excited ultraviolet lamp systems configured to uniformly irradiate with ultraviolet radiation a substrate positioned within a processing space of the microwave chamber. In the present invention, the substrate is positioned in the processing space near a microwave-excited plasma lamp for increasing the intensity of the ultraviolet radiation. Further, the present invention incorporates a reflector capable of providing a relatively uniformly irradiance in a surrounding relationship relative to, or about the circumference of, the substrate. Further, the present invention isolates the substrate with an ultraviolet-transmissive conduit such that fragile substrates can be accommodated and yet a sufficient air flow provided to cool the microwave generators and plasma lamp. Further, the present invention permits the substrate to enter the microwave chamber and to travel within the processing space without substantial microwave leakage from the chamber. Further, the well-defined relative positions of the reflector, the substrate, and the plasma lamp within the processing space of the microwave chamber provide a precise and reproducible pattern of ultraviolet radiation that surrounds the substrate.

Figure 1:
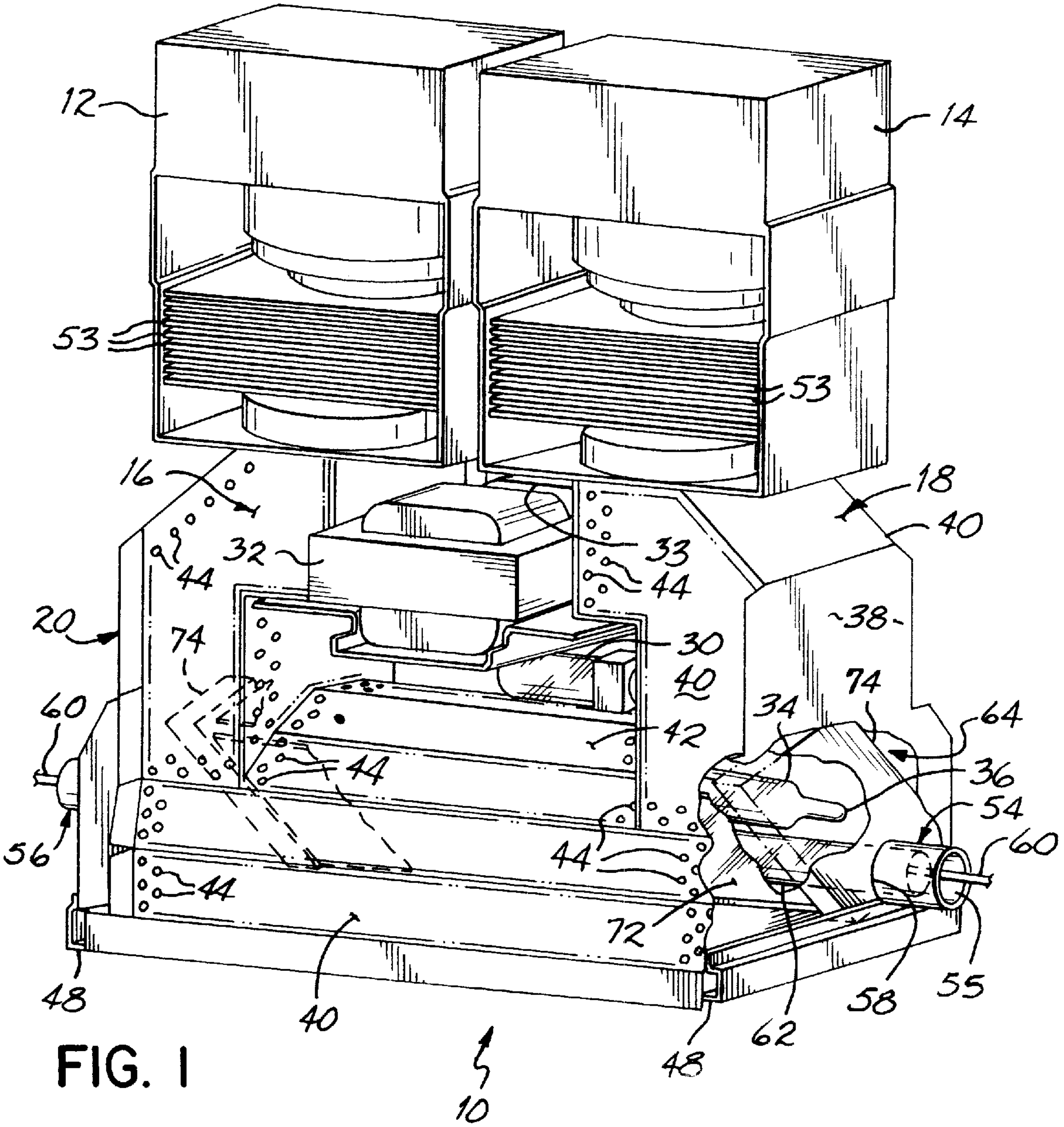
FIG. 1 is a perspective side view of an ultraviolet lamp system of the present invention.
Figure 2:
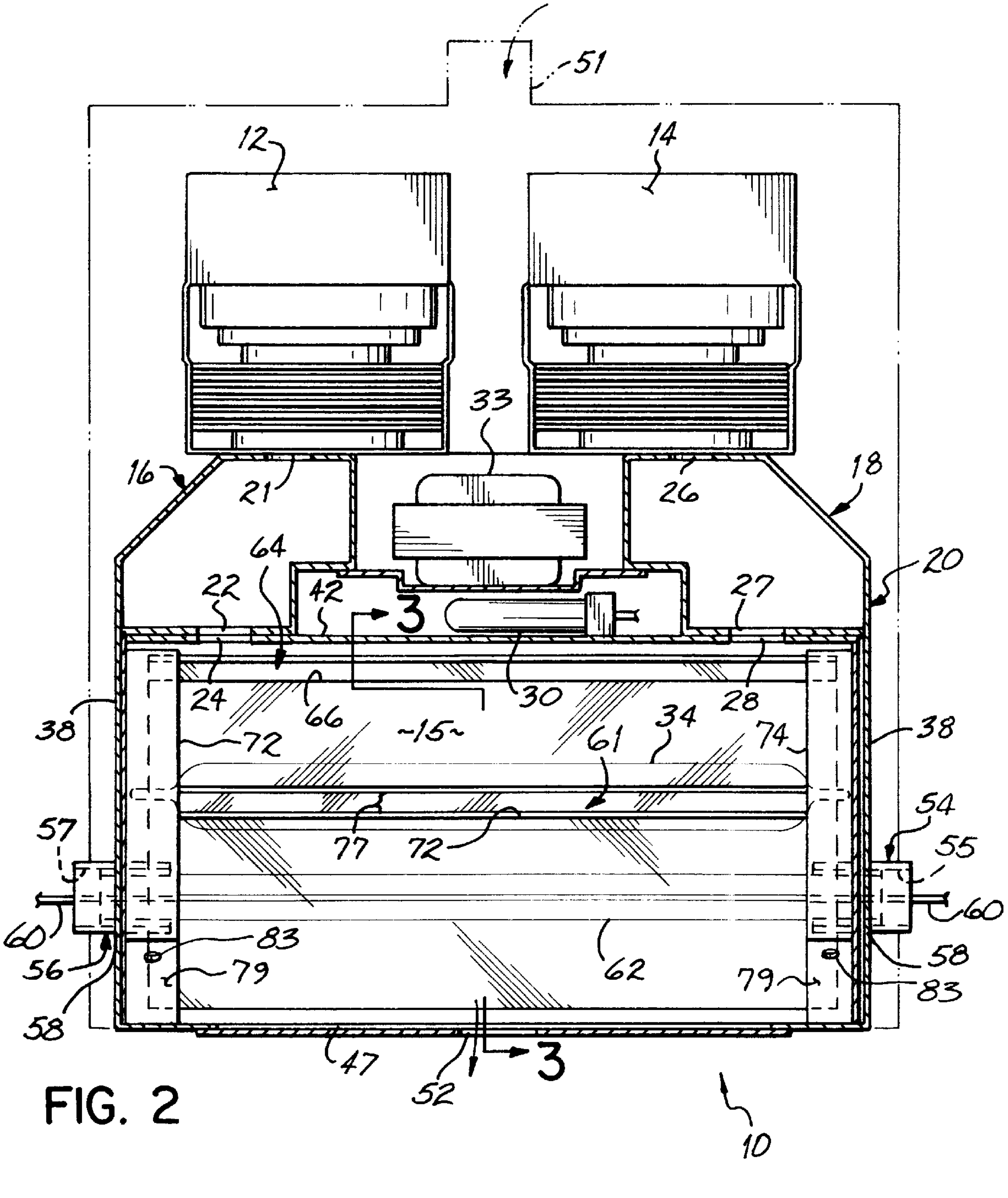
FIG. 2 is a partial longitudinal cross-sectional view of an ultraviolet lamp system taken along line 2—2 of FIG. 1.

With reference to FIGS. 1 and 2, a microwave-excited ultraviolet lamp system of the present invention is indicated generally by reference numeral 10. Lamp system 10 includes a pair of microwave generators 12 and 14, illustrated as magnetrons, mechanically mounted by a respective one of a pair longitudinally-spaced waveguides 16 and 18 to a longitudinally-extending microwave chamber, indicated generally by reference numeral 20. A pair of transformers 32 and 33 (FIG. 2 shows only transformer 33) are electrically coupled to a respective one of the microwave generators 12 and 14 for energizing filaments of the microwave generators 12 and 14 as understood by those of ordinary skill in the art. To prevent cross-coupling when the lamp system 10 is operating, the operating frequencies of the two microwave generators 12 and 14 should be offset by a small amount. By way of specific example but not limitation, the two microwave generators 12 and 14 may operate at respective frequencies of about 2470 MHz and about 2445 MHz, which represents a frequency offset of 25 MHz, and may have individual power ratings of about 3 kW. While a pair of microwave generators 12 and 14 is illustrated and described herein, the lamp system 10 may include only a single microwave generator without departing from the spirit and scope of the present invention.

Waveguide 16 includes an inlet port 21 coupled with microwave generator 12 and an outlet port 22 which is aligned and coupled for microwave transmission with an opening 24 provided in the microwave chamber 20. Similarly, waveguide 18 includes an inlet port 26 coupled with microwave generator 14 and an outlet port 27 which is aligned and coupled for microwave transmission with an opening 28 provided in the microwave chamber 20. Microwave energy from the microwave generators 12 and 14 is directed via waveguides 16 and 18 to an interior space 15 of the microwave chamber 20 through the openings 24 and 28. Microwave energy is deposited with a three-dimensional density distribution within the microwave chamber 20 as understood by those of ordinary skill in the art.

A plasma lamp 34 is positioned longitudinally within the microwave chamber 20. Opposite ends 36 of plasma lamp 34 are supported within the microwave chamber 20 as understood by those of ordinary skill in the art. Plasma lamp 34 comprises a hermetically sealed, longitudinally-extending envelope or tube filled with a gas mixture. Plasma lamp 34 does not require either electrical connections or electrodes for its operation. The plasma lamp 34 is formed of an ultraviolet-transmissive material that is an electrical insulator, such as vitreous silica or quartz, so that the plasma lamp 34 is electrically isolated from other structures in the microwave chamber 20. Microwave energy provided by the microwave generators 12 and 14 guides excited atoms in the gas mixture within plasma lamp 34 to initiate and, thereafter, sustain the plasma therein. A starter bulb 30 is provided to assist in initiating a plasma within plasma lamp 34 as understood by those of ordinary skill in the art. By adjusting the shape of microwave chamber 20 and the power level of microwave generators 12 and 14, the density distribution of the microwave energy is selected to excite atoms in the gas mixture along the entire longitudinal dimension of the plasma lamp 34. Once the plasma is initiated, the intensity of the radiation output by the plasma lamp 34 depends upon the microwave power provided to microwave chamber 20 by microwave generators 12 and 14.

The gas mixture inside plasma lamp 34 has an elemental composition selected to produce photons having a predetermined distribution of wavelengths of radiation when the gas atoms are excited to a plasma state. For ultraviolet treating applications, the gas mixture may comprise a mercury vapor and an inert gas, such as argon, and may include trace amounts of one or more elements such as iron, gallium, or indium. The mercury vapor is provided by the vaporization of a small quantity of mercury that is solid at room temperature. The spectrum of radiation output by a plasma excited from such a gas mixture includes highly intense ultraviolet and infrared spectral components. As used herein, radiation is defined as photons having wavelengths ranging between about 200 nm to about 2000 nm, ultraviolet radiation is defined as photons having wavelengths ranging between about 200 nm to about 400 nm, and infrared radiation is defined as photons having wavelengths ranging between about 750 nm to about 2000 nm.

As best understood with reference to FIG. 1, microwave chamber 20 includes a pair of generally vertical opposite end walls 38 and a pair of generally vertical opposite side walls 40 extending longitudinally between the end walls 38 and on opposite sides of the plasma lamp 34. A segmented, domed wall 42 connects intermediate portions of the side walls 40 between openings 24 and 28. Walls 38, 40, and 42 are each perforated with a plurality of openings 44 that permit the free flow of air. It is understood that the walls of microwave chamber 20 can be configured differently without departing from the spirit and scope of the present invention. In particular, the configuration of the domed wall 42 can be varied to alter or tune the density distribution of microwave energy within microwave chamber 20. Microwave chamber 20 is constructed of a suitable metal, such as a stainless steel, that confines the microwave energy to the interior space 15 of the microwave chamber 20.

Figure 3:
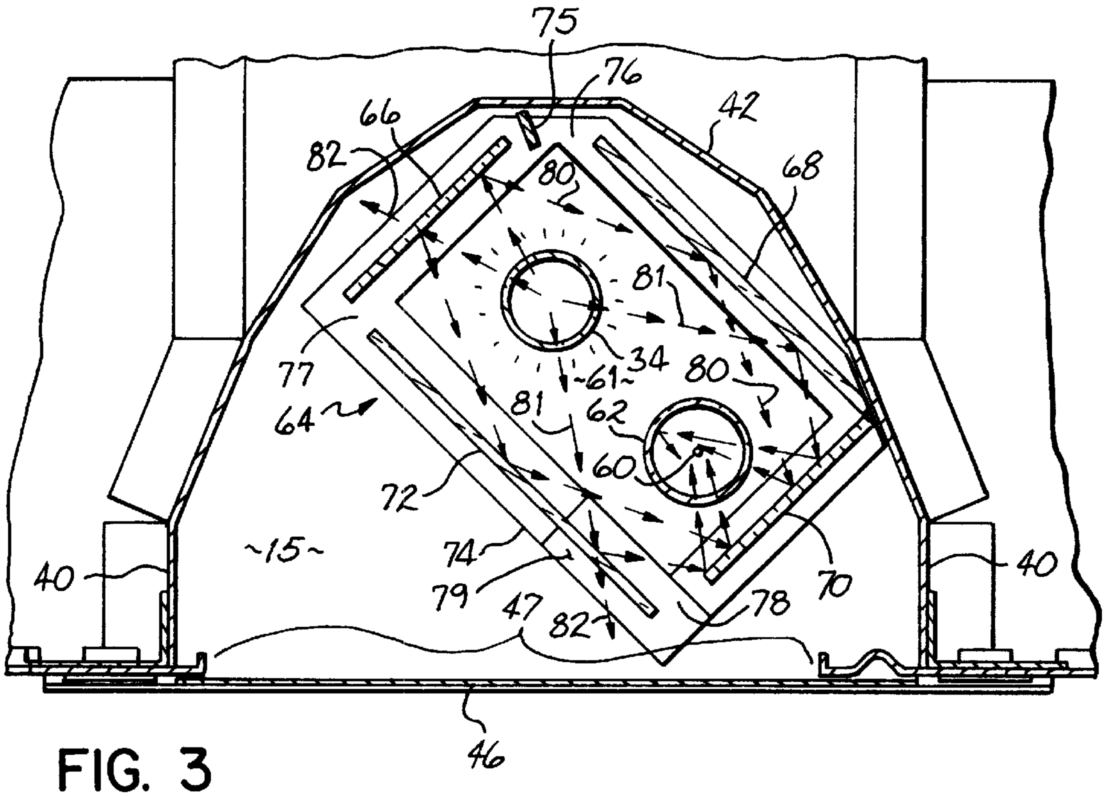
FIG. 3 is a cross-sectional view of the ultraviolet lamp system of FIG. 1 taken along line 3—3 of FIG. 2, showing one embodiment of a reflector for use in the lamp system of FIG. 1.

As best shown in FIG. 3, a cover 46 is mounted to a pair of generally horizontal flanges 48 that extend inwardly from the chamber side walls 40. Cover 46 is removable to reveal an access opening 47 for entry into interior space 15 of the microwave chamber 20. Interior space 15 must be accessed for maintenance purposes, such as servicing or replacing plasma lamp 34 or other objects within the interior space 15 of the microwave chamber 20. Cover 46 has a sealing engagement with access opening 47 that prevents significant amounts of either radiation or microwave energy from being emitted through access opening 47.

With reference to FIG. 2, lamp system 10 is mounted within an enclosure 50, shown in phantom, having a configuration as recognized by those of ordinary skill in the art. The housing 50 includes an air inlet 51 and an air outlet 52 provided in cover 46. A flow of a pressurized gas, such as air, into air inlet 51 is used to regulate the operating temperature of the microwave generators 12 and 14 and the operating temperature of the plasma lamp 34. Microwave generators 12 and 14 each include a plurality of circumferential fins 53. The fins 53 are operable for increasing the efficiency for conducting heat away from the microwave generators 12 and 14 and enhance the available surface area for convective cooling by the flow of air. A fan (not shown) is generally provided as a means for forcing a pressurized flow of air into enclosure 50, over microwave generators 12 and 14, through openings 44 into the microwave chamber 20, and out of enclosure 50 through outlet 52. The pressurized flow of air provides a constant exchange of cool air for heated air within the enclosure 50 and reduces maintenance caused by overheated components. Those skilled in the art would recognize that microwave-excited ultraviolet lamp systems, such as lamp system 10, generate significant amounts of heat that must be eliminated to avoid unacceptably high operating temperatures.

A microwave choke 54 is attached to an inlet port 55 provided in one of the end walls 38 of the microwave chamber 20. A microwave choke 56 is attached to an outlet port 57 provided in the opposite end wall 38. The ports 54 and 55 and the interior passageways 58 of microwave chokes are generally aligned longitudinally. Microwave chokes 54 and 56 are hollow, tubular members with a length and diameter chosen, as would be familiar to those of ordinary skill in the art, for preventing a significant amount of microwave energy from leaking outwardly from the interior space 15 of the microwave chamber 20 through ports 55 and 57. By way of example, and not by way of limitation, microwave chokes 54 and 56 may have a length of about 1 inch and an inner diameter of about 0.75 inches.

Microwave chokes 54 and 56 are attached flush with the ports 55 and 57, respectively, such that no portion of either microwave choke 54 and 56 protrudes a significant distance into the interior space 15 of the microwave chamber 20. Suitable microwave chokes 54 and 56 are constructed of a metal alloy, such as a stainless steel, and include, but are not limited to, waveguide chokes, quarter-wave stub chokes, or corrugated chokes in combination with a resistive choke. In certain embodiments of the present invention, microwave chokes 54 and 56 may be omitted from parts 55 and 57 without departing from the spirit and scope of the present invention.

Lamp system 10 is used for the treatment of a non-conductive substrate 60 which is at least partially covered by a coating, such as an ultraviolet-curable coating. Substrate 60 may be a cable which is at least partially covered by a coating or, more specifically, a fiber optic cable which is at least partially covered by a coating. As used herein, treatment is defined as curing, heating, or any other process that alters a physical property of a coating as a result of exposure to ultraviolet radiation.

Substrate 60 travels within or through the interior space 15 via inlet port 55 and outlet port 57 of the microwave chamber 20. Those of ordinary skill will appreciate that substrate 60 may both enter and exit the interior space 15 through one of either the inlet port 55 or the outlet port 57 such that microwave chamber 20 can include only one of inlet port 55 or outlet port 57 without departing from the spirit and scope of the present invention. During transfer within or through the interior space 15 of the microwave chamber 20, the substrate 60 is continuously irradiated with ultraviolet radiation while positioned in a longitudinally-extending processing space 61. Processing space 61 comprises a portion of the interior space 15 having an irradiance or flux density of ultraviolet radiation. Because substrate 60 is positioned directly within the processing space 61 of the microwave chamber 20, the separation distance between the plasma bulb 34 and the substrate 60 is minimized. Because the intensity of ultraviolet radiation per unit measure of microwave energy delivered to the substrate 60 is optimized, the microwave generators 12 and 14 can be operated at a reduced power level for exciting plasma lamp 34 to deliver a given intensity of ultraviolet energy. Alternatively, the intensity of the ultraviolet radiation can be optimized such that substrate 60 may be transferred through or within the microwave chamber 20 at a higher rate for enhancing the treatment throughput of the lamp system 10.

Because substrate 60 is physically positioned inside the microwave chamber 20 during irradiation, a chamber outlet covered by a metallic mesh screen is not required in one of the walls 38, 40 and 42 of the microwave chamber 20 for transmitting ultraviolet radiation to an externally-positioned substrate and for confining the microwave energy to the interior of the microwave chamber 20. As a result, the microwave chamber 20 is robust, tightly sealed against microwave and ultraviolet leakage, and does require special structure to prevent microwave leakage while irradiating a substrate with ultraviolet radiation.

In an aspect of the present invention, the passageways 56 of the substrate inlet port 54 and the substrate outlet port 55 and the respective one of the openings 58 in end walls 38 are generally aligned with an ultraviolet-transmissive conduit 62 positioned within the microwave chamber 20. Conduit 62 extends longitudinally between the end walls 38 and is supported at opposite ends by the interior of passageways 56 of ports 54 and 55. Conduit 62 encloses the substrate 60 during the longitudinal transfer of substrate 60 within the interior space 15 of the microwave chamber 20. Conduit 62 is formed of an electrically-insulating material that is highly transmissive of ultraviolet radiation, such as a quartz or a vitreous silica. Conduit 62 prevents extraneous forces from acting on substrate 60, such as the forced air currents directed into the microwave chamber 20 for cooling the plasma lamp 34. This isolation ability is particularly important if substrate 60 is fragile or otherwise prone to damage. However, the conduit 62 may be omitted, such that substrate 60 is not enclosed while in interior space 15, without departing from the spirit and scope of the present invention.

A longitudinally-extending reflector, indicated generally by reference numeral 64, is positioned within the microwave chamber 20. As best shown in FIG. 3, reflector 64 includes a quartet of longitudinally-extending, rectangular reflector panels 66, 68, 70, and 72. The reflector panels 66, 68, 70, and 72 are mounted in a spaced rectangular arrangement via a pair of brackets 74,attached to opposed end walls 38 of the microwave chamber 20. Brackets 74 are preferably formed of an electrically-insulating material, such as a thermally-stable polymer and, more specifically, a fluoropolymer. Opposite ends of each reflector panel 66, 68, 70, and 72 are received by slots (not shown) in each bracket 74. Reflector panels 66, 68, 70, and 72 have a spaced relationship relative to the plasma lamp 34 and a spaced relationship relative to the ultraviolet-transmissive conduit 62 enclosing substrate 60 such that the portion of interior space 15 between the reflector panels 66, 68, 70, and 72 at least partially defines the processing space 61. Microwave energy provided by microwave generators 12 and 14 is readily transmitted through the reflector panels 66 and 68 for initiating a plasma from the gas mixture in plasma lamp 34 and for sustaining the plasma for the duration of a heating or curing operation. Gaps 76, 77 and 78 are provided between the reflector panels 66, 68, 70, and 72 for permitting a flow of relatively cool air to cool the plasma lamp 34. Diverter baffle 75 is provided to preferentially direct a flow of relatively cool air through gap 76 toward plasma lamp 34.

The reflector panels 66, 68, 70, and 72 are configured with an inclined arrangement relative to the side walls 40 of the microwave chamber 20 so that the plasma lamp 34 can be physically accessed from access opening 47 when cover 46 is removed. As best shown in FIGS. 2 and 3, each bracket 74 includes a removable portion 79 that is attached by fasteners 83. The fasteners 83 are preferably formed of an electrically insulating material, such as a ceramic. To remove reflector panel 72, fasteners 83 are loosened to free the removable portion 79 for detachment from each bracket 74 and reflector panel 72 is slidingly removed from the corresponding slots in brackets 74. With reflector panel 72 removed, the path is unobstructed from the access opening 47 to objects, such as the plasma lamp bulb 34, specifically within the processing space 61 and from the access opening 47 to objects generally within the interior space 15 and within the processing space 61.

The reflector panels 66, 68, 70, and 72 are preferably formed of a radiation-transmissive material, such as a borosilicate glass or, more specifically, a Pyrex® glass. Flat plates of Pyrex® glass suitable for use as reflector panels 66, 68, 70, and 72 are commercially available from Corning Inc. (Corning, N.Y.). Alternatively, reflector panels 66, 68, 70, and 72 may be formed of any material having suitable reflective and thermal properties and, in particular, reflector panels 66, 68, 70, and 72 may be constructed of a metal and need not be radiation-transmissive or infrared-transmissive if integrally formed as a portion of the microwave chamber 20.

For use in the ultraviolet lamp system 10, reflector 64 is operable for at least partially transmitting, reflecting or absorbing photons of specific wavelengths. Specifically, reflector 64 is capable of preferentially reflecting photons of ultraviolet radiation, indicated diagrammatically by arrows 80, from the spectrum of emitted radiation, indicated diagrammatically by arrows 81, emanating from the plasma lamp 34 and preferentially transmitting absorbing photons of infrared radiation, where transmission of infrared radiation is indicated diagrammatically by arrows 82. The preferential transmission and reflection can be provided by methods known to those of ordinary skill, such as applying a dichroic coating to reflector panels 66, 68, 70, and 72. Due to the nature of the reflections and multiple reflections, the reflector 64 (FIG. 3) provides a flood pattern of ultraviolet radiation 80 reflected to substrate 60, rather than a focused pattern and, in particular, provides a substantially uniform flood pattern of ultraviolet irradiation 80 reflected about the circumference of, or in a surrounding relationship relative to, the substrate 60.

As shown in FIG. 3, a significant portion of the infrared radiation 82 is transmitted through the reflector 64 and channeled to the peripheries of the microwave chamber 20 away from the vicinity of the reflector 64. As a result, the ultraviolet radiation 80 reflected by reflector 64 toward the substrate 60 is not accompanied by a significant intensity of infrared radiation 82. Therefore, substrate 60 remains at a relatively low temperature despite being exposed to a significant intensity of ultraviolet radiation 82. Chamber walls 38, 40 and 42 are capable of absorbing the photons of infrared radiation 82 and dissipating the energy thermally.

Figure 3A:
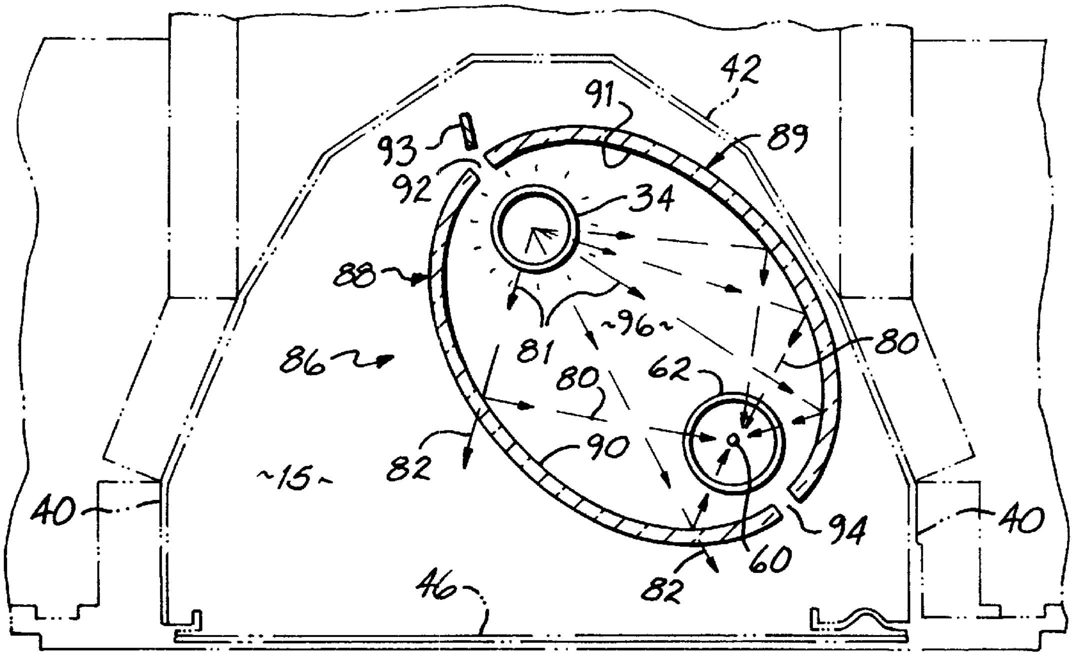
FIG. 3A is a cross-sectional view similar to FIG. 3 of an alternative embodiment of a reflector of the present invention for use in the lamp system of FIG. 1.

Using like reference numerals for like elements discussed with reference to FIGS. 1, 2 and 3, an alternative embodiment of a reflector, indicated generally by reference numeral 86, in accordance with the present invention, is shown in FIG. 3A. Reflector 86 includes a pair of longitudinally extending reflector panels 88 and 89 that are mounted within the microwave chamber 20 as understood by those of ordinary skill in the art on brackets (not shown) similar to brackets 74 (FIGS. 1 and 2). Each reflector panel 88 and 89 has a concave inner surface 90 and 91, respectively, which is generally shaped as a portion of an ellipse having two spaced foci. The concave inner surfaces 90 and 91 of reflector panels 88 and 89 have an opposing and facing relationship and are positioned with a spaced relationship relative to the plasma lamp 34 and relative to the ultraviolet-transmissive conduit 62 housing the substrate 60. A processing space 96 is at least partially defined between reflector panels 88 and 89 and defines a portion of interior space 15 operable for irradiating substrate 60 with ultraviolet radiation. The reflector panels 88 and 89 are preferably formed of a radiation-transmissive material, such as a borosilicate glass and, more specifically, Pyrex® glass. Gaps 92 and 94 are provided between the reflector panels 88 and 89 for permitting a flow of air to cool the plasma lamp 34. Diverter baffle 93 is provided to preferentially direct the flow of relatively cool air through gap 92 toward plasma lamp 34.

The reflector panels 88 and 89 are arranged such that the respective concave surfaces 90 and 91 generally share common foci to effectively give reflector 86 a full elliptical geometrical shape. Reflector 86 operates in the same manner as discussed above with regard to reflector 64 (FIG. 3) for delivering a relatively uniform irradiance of ultraviolet radiation 80 about the circumference of, or in a surrounding relationship relative to, the substrate 60. However, the ultraviolet radiation is focused about the substrate 60 as compared with the flood of radiation provided by reflector 64 (FIG. 3). Infrared radiation 82 is preferentially transmitted through the reflector 86 and absorbed by the walls 38, 40 and 42 of the microwave cavity 20 for subsequent thermal dissipation. Alternatively, infrared radiation 82 may be absorbed by the reflector 86 and thermally dissipated.

The reflector panels 88 and 89 have a spaced relationship with respect to the plasma lamp 34 and a spaced relationship relative to the substrate 60. The substrate 60 is located near one focus of the ellipse defined by reflector panels 90 and 91, and the plasma lamp 34 is located near the other focus of the ellipse. As a result of the arrangement of plasma lamp 34 and substrate 60, a plurality of substantially focused longitudinal lines of ultraviolet radiation 82 from the plasma lamp 34 is delivered directly and indirectly by reflection from the reflector in a uniform fashion about the circumference of the substrate 60. The lines of ultraviolet radiation 82 are also uniformly delivered along the entire longitudinal dimension of the portion of the substrate 60 positioned within the processing space 96.

A known characteristic of an elliptical reflector is that a ray of radiation emitted from a source positioned at one focus will pass through the other focus after a single reflection. Thus, a light source that approximates a line source, such as plasma lamp 34, that is positioned longitudinally at or near one focus of an elliptical reflector will deliver a substantially focused line of radiation to a substrate, such as substrate 60, positioned at or near the second focus. The radiation will be uniformly distributed about the circumference of the substrate.

Reflector 86 is also positioned relative to the side walls 40 and domed wall 42 of the microwave chamber 20 to permit access through the access opening 47 to the plasma lamp 34 in the processing space 96 and other objects within the interior space 15 and the processing space 96 of the microwave chamber 20. To that end, reflector panel 88 may be removably detached from the brackets (not shown) supporting panel 88 within the microwave chamber 20. After cover 46 is removed, reflector panel 88 is repositioned so that it does not obstruct the path from the access opening 47 in the microwave chamber 20 to the plasma lamp 34.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. For example, the present invention could be used to irradiate fluids flowing within an ultraviolet-transmissive flow tube through the interior of the microwave chamber. In its broader aspects, the present invention is not limited to ultraviolet irradiation but could irradiate substrates positioned within the microwave chamber with radiation having visible wavelengths or infrared wavelengths. The invention in its broader aspects is therefore not limited to the specific details, representative apparatus and method, and illustrative examples shown and described. Accordingly, departures may be made from such details without departing from the spirit or scope of applicants general inventive concept.

Having described the invention, we claim:

1. An ultraviolet radiation generating system for treating a coating on a substrate, comprising:

a microwave chamber having a processing space and an inlet port capable of permitting the substrate to be positioned in said processing space, said microwave chamber being substantially closed to emission of microwave energy therefrom;

a longitudinally-extending plasma lamp mounted within said processing space of said microwave chamber;

a microwave generator coupled to said microwave chamber for exciting said plasma lamp to emit ultraviolet radiation within said chamber for irradiating the substrate in said processing space; and a reflector mounted within said microwave chamber configured to reflect ultraviolet radiation from said plasma lamp for irradiating the substrate in said processing space, said reflector including a plurality of longitudinally-extending rectangular reflector panels each arranged with a respective reflecting surface facing said plasma lamp for providing a flood pattern of ultraviolet radiation in a surrounding relationship about a circumference of the cable.

2. The ultraviolet radiation generating system of claim 1 wherein said microwave chamber further comprises an outlet port capable of permitting the substrate to travel through said microwave chamber at least partially within said processing space between said inlet port and said outlet port.

3. The ultraviolet radiation generating system of claim 1 wherein the substrate is a cable.

4. The ultraviolet radiation generating system of claim 3 wherein the cable is a fiber optic cable.

5. The ultraviolet radiation generating system of claim 1 wherein said reflector panels are configured to provide at least one air flow inlet and at least one air flow outlet into said processing space.

6. The ultraviolet radiation generating system of claim 1 further comprising a pair of spaced ceramic brackets attached to said microwave chamber, said brackets supporting said reflector.

7. An ultraviolet radiation generating system for treating a coating on a fiber optic cable, comprising:

a microwave chamber having a processing space, an inlet port and an outlet port capable of permitting the cable to be positioned in said processing space, said microwave chamber being substantially closed to emission of microwave energy therefrom;

a first microwave choke attached to said inlet port and a second microwave choke attached to said outlet port, said first and second microwave chokes capable of preventing emission of microwave energy from said inlet and outlet ports, respectively;

a longitudinally-extending plasma lamp mounted within said processing space of said microwave chamber; and, a microwave generator coupled to said microwave chamber for exciting said plasma lamp to emit ultraviolet radiation within said chamber for irradiating the cable in said processing space; and a longitudinally-extending reflector mounted within said microwave chamber capable of reflecting a portion of the ultraviolet radiation for irradiating the cable in said processing space.

8. The ultraviolet radiation generating system of claim 7 wherein said reflector is capable of reflecting a focused pattern of ultraviolet radiation in a surrounding relationship to the fiber optic cable.

9. The ultraviolet radiation generating system of claim 7 wherein said reflector is configured to reflect a flood pattern of ultraviolet radiation from said plasma lamp in a surrounding relationship to a circumference of the fiber optic cable.

10. An ultraviolet radiation device having a processing space and capable of irradiating an object positioned at least partially within said processing space, said device comprising:

a plasma lamp positioned within said processing space in a spaced relationship relative to the object, said plasma lamp capable of providing a source of ultraviolet radiation when operative; and a longitudinally-extending reflector positioned about said processing space and separate from said plasma lamp, said reflector having a spaced relationship relative to said plasma lamp and a spaced relationship relative to said object, said reflector configured to reflect a flood pattern of ultraviolet radiation from said plasma lamp in a surrounding relationship about a circumference of the object for irradiating the object in said processing space.

11. The ultraviolet radiation device of claim 10 wherein the object is traveling through said processing space.

12. A method of treating a coating on a substrate within a processing space of a microwave chamber having a plasma lamp mounted within the processing space and a reflector mounted within the processing space with a spaced relationship to the plasma lamp, comprising:

moving the substrate through the processing space;

exciting the plasma lamp with microwave energy to emit ultraviolet radiation;

reflecting ultraviolet radiation from the plasma lamp in a flood pattern with a surrounding relationship about a circumference of the substrate; and treating the substrate moving within the processing space with the ultraviolet radiation and the reflected ultraviolet radiation.

13. The method of claim 12 further comprising enclosing the substrate within an ultraviolet-transmissive conduit when the substrate is positioned within the processing space of said microwave chamber.

14. The ultraviolet radiation device of claim 1, wherein said reflector includes at least four longitudinally-extending reflector panels.

15. The ultraviolet radiation device of claim 10, further comprising:

a microwave chamber having said processing space and an inlet port capable of permitting the object to be positioned in said processing space, said microwave chamber being substantially closed to emission of microwave energy therefrom; and a microwave generator coupled to said microwave chamber for exciting said plasma lamp to emit ultraviolet radiation within said chamber for irradiating the object in said processing space.

* * * * *

UNITED STATES PATENT AND TRADEMARK OFFICE

CERTIFICATE OF CORRECTION

PATENT NO. : 6,559,460 B1
DATED : May 6, 2003
INVENTOR(S) : Patrick Keogh et al.

It is certified that error appears in the above-identified patent and that said Letters Patent is hereby corrected as shown below:

Column 10,
Line 23, change "cable" to -- substrate --.

Signed and Sealed this

Twenty-third Day of December, 2003

JAMES E. ROGAN
*Director of the United States Patent and Trademark Office*